(12) United States Patent
Wang

(10) Patent No.: US 7,776,819 B2
(45) Date of Patent: Aug. 17, 2010

(54) TARGETED DRUG DELIVERY OF PAIN AND ADDICTION THERAPIES USING OPIOID RECEPTOR-MEDIATED INTERNALIZATION

(75) Inventor: Zaijie Jim Wang, Oak Park, IL (US)

(73) Assignee: The Board of Trustees of the University of Illinois, Chicago, IL (US)

( * ) Notice: Subject to any disclaimer, the term of this patent is extended or adjusted under 35 U.S.C. 154(b) by 530 days.

(21) Appl. No.: 11/817,431

(22) PCT Filed: Mar. 2, 2006

(86) PCT No.: PCT/US2006/007323

§ 371 (c)(1),
(2), (4) Date: Oct. 19, 2007

(87) PCT Pub. No.: WO2006/096426

PCT Pub. Date: Sep. 14, 2006

(65) Prior Publication Data

US 2008/0227722 A1    Sep. 18, 2008

Related U.S. Application Data

(60) Provisional application No. 60/658,975, filed on Mar. 3, 2005.

(51) Int. Cl.
*A61K 38/00* (2006.01)
*C07K 14/00* (2006.01)
(52) U.S. Cl. ............................ 514/2; 530/300; 977/757
(58) Field of Classification Search ........................ None
See application file for complete search history.

(56) References Cited

U.S. PATENT DOCUMENTS 6,359,111 B1    3/2002    Meyer et al.

OTHER PUBLICATIONS

Ambo et al., "Dermorphin Tetrapeptide Analogues with 2',6'-dimethylphenylalanine (Dmp) Substituted for Aromatic Amino Acids have High mu Opioid Receptor Binding and Biological Activities", Bioorganic & Medicinal Chemistry Letters 2003 13:1269-1272.

Wang et al., "Pronociceptive Actions of Dynorphin Maintain Chronic Neuropathic Pain", The Journal of Neuroscience 2001 21(5):1779-1786.

Wang et al., "Reversal of morphine antinociceptive tolerance by acute spinal inhibitiobn of Ca2+/calmodulin-dependent protein kinase II", European Journal of Pharmacology 2003 465:199-200.

Wang et al., "Tolerance to morphine at the mu-opioid receptor differentially induced by cAMP-dependent protein kinase activation and morphine", European Journal of Pharmacology 2000 389:165-171.

Zalipsky et al., "Poly(ethylene glycol)-Grafted Lioposomes with Oligopeptide or Oligosaccharide Ligands Appended to the Termini of the Polymer Chains", Bioconjugate Chem. 1997 8:111-118.

*Primary Examiner*—Anand U Desai
(74) *Attorney, Agent, or Firm*—Licata & Tyrrell P.C.

(57) ABSTRACT

Drug delivery is targeted to new opioid receptors using receptor-mediated internalization. Dermorphin was successfully conjugated to DSPE-PEG3400 without affecting the affinity to its receptor. The synthesized conjugate was inserted into preformed sterically stabilized liposomes to obtain dermorphin-grafted SSL. DSPE-PEG34Qo-dermorphin and dermorphin-SSL retained their affinity and selectivity for MOR. Moreover, dermorphin-SSL and encapsulated probes were taken up by CHO-hMOR cells, but not by naive CHO cells or very closely related CHO-hDOR cells. Dermorphin-SSL can be used to deliver drugs to the intracellular component of intended cells with high fidelity. Therefore, dermorphin-SSL is useful to carry pharmaceutical agents to achieve region-specific delivery of analgesics and/or to attenuate side effects associated with opioids.

7 Claims, 7 Drawing Sheets

Figure 1:
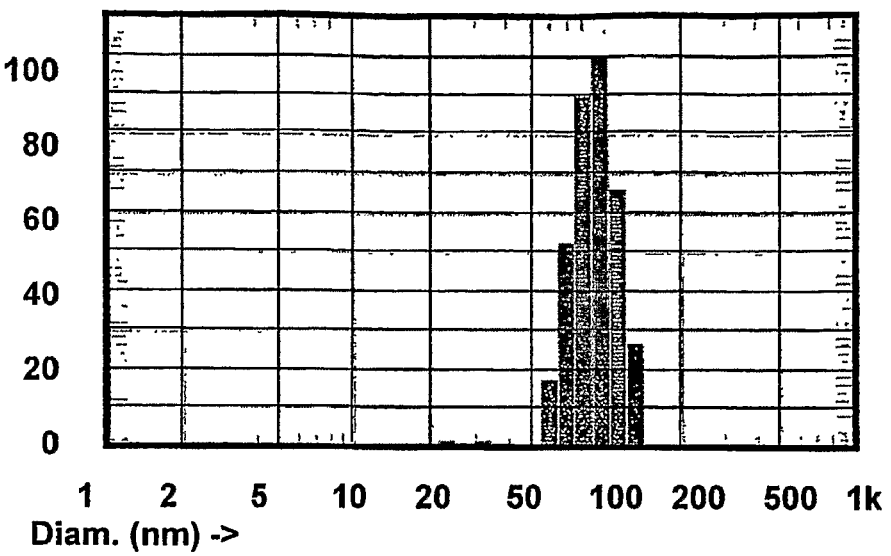

TARGETED DRUG DELIVERY OF PAIN AND ADDICTION THERAPIES USING OPIOID RECEPTOR-MEDIATED INTERNALIZATION

CROSS REFERENCE TO RELATED APPLICATIONS

The present application is the National Stage entry of PCT/US2006/007323, filed Mar. 2, 2006, which claims priority to U.S. Provisional Application No. 60/658,975 filed Mar. 3, 2005.

BACKGROUND

One of the most significant health problems is the inadequate control of pain, especially chronic pain that is associated with many diseases such as cancer, back pain, arthritis, diabetic neuropathy, and other conditions. Postoperative pain affects up to 53 M patients in the United States alone. Despite most patients receiving some form of pain management, over half of these patients still experience inadequate pain relief. It is estimated that annual cost for health care and lost productivity related to pain is over $100 billion dollars in the United States. Impact of pain to society can be measured not only in economic numbers, but more importantly also by the patients' suffering. More than 50 million Americans live partially or totally disabled by chronic pain. There is currently no nationally accepted consensus for the treatment of chronic pain not due to cancer, yet the economic and social costs of chronic pain are substantial, with estimates ranging in the tens of billions of dollars annually. Although other areas of the world may have different protocols for pain relief, pain is a universal problem.

Morphine and other opioids have been widely used clinically for the treatment of pain. Tolerance including attenuated analgesic effect after repeated administration of opioids is well documented in clinical practice and causes inadequate treatment of pain. Pharmacological studies have established that morphine-induced analgesia, tolerance, and dependence are primarily mediated by mu opioid receptors (MOR). There have been many potential targets proposed to alleviate tolerance but many targets are intracellular. In addition, achieving cell-specific delivery presents a challenge to traditional pharmacological approach.

Opioid analgesics and traditional NSAIDs remain a mainstay of pain treatment; however, use of opioids for chronic pain leads to development of drug tolerance and drug dependence. The publications endorsed by AAPM and APS state that opioids sometimes called "narcotic analgesics," are an essential part of a pain management plan.

Impediments to the use of opioids include concerns about addiction, respiratory depression and other side effects, tolerance, diversion, and fear of regulatory action.

Opioid addiction has physiological (sudden absence of the drug produces a withdrawal syndrome) and psychological components (the urge to use opioids to achieve euphoria, sedation and the like). Dependence is the term referring to physiological response at withdrawal. A decreased responsiveness to the pharmacological effects of a drug resulting from previous exposure is called tolerance.

There are cellular opioid receptor subtypes. In general an opioid reacts with all receptor subtypes in some way. The following basic principle holds since the binding of an opioid to the different receptor populations is variable, the affinity of an opioid to a subtype of receptor manifests itself in the dependant clinical effects.

| Function | Receptor | | |
|---|---|---|---|
| | μ | κ | δ |
| Analgesia cerebral | + | − | + |
| Spinal | + | + | + |
| Vigilance | − | ↓ | ↑ |
| Respiratory drive | ↓ | − | ↑ |
| Heart rate | ↓ | | ↑ |
| Cardiovascular tonus | − | ↓ | − |
| Endorcrine effects | + | − | − |
| Diuresis | ↓ | ↑ | − |
| Constipation | + | − | − |
| Euphoria | + | − | − |
| Dysphoria | − | + | + |
| Pupil size | ↓ | ↓ | ↑ |
| Nausea | + | − | + |
| Muscular rigidity | ↑ | ↓ | ↑ |

− = no effect, + = effect, ↑ = increasing, ↓ = decreasing

Finding a method and/or agent to prevent and/or reverse opioid tolerance would provide better pain control in a large population of patients who are not adequately treated with opioid analgesics alone. Such a method/agent will also have use in treating opioid addiction.

Many cellular pathways (including several studied in the inventor's lab) have been proposed to stop opioid tolerance and/opioid dependence. However, most of these pathways have not been developed into medications that can help patients, most commonly due to the following reasons:

the targets are intra-cellular making bioavailability a difficult issue to overcome for potential drugs;

most targets are ubiquitously expressed therefore inhibiting such targets may produce too many unnecessary side effects; and some of the most selective inhibitors for these intracellular pathways are peptides, making delivery to the target especially difficult.

New compounds boasting novel modes of delivery are desperately needed in this developing market.

SUMMARY

A novel pharmacotherapeutic approach for treatment of pain, opioid tolerance and opioid addiction prevents and/or reverses opioid tolerance and provides better pain control in a large population of patients who are being treated with opioids.

Targeted drug delivery to the intracellular component is accomplished through the combination of receptor-mediated internalization and pharmaceutical carrier systems that enhance the bioavailability of water-insoluble or non-cell permeable drugs (including peptides) by using nanoparticles such as sterically stable liposome constructs, micelles or polymer devices.

Ligand-grafted sterically stabilized liposomes (SSL) have been successfully used as an active-targeting drug delivery system that can target both cell surface and intracellular molecules in a specific cell population. Ligands can specifically bind to the corresponding receptor on the cell membrane with high affinity and selectivity. In the case of MOR, a member of G protein coupled receptors, the drug encapsulated in SSL can be delivered to the intracellular compartment via receptor-mediated endocytosis, since MOR is known to internalize with certain opioid drugs. Dermorphin (a selective MOR agonist)-grafted SSL (DPD-SSL) was actively and selectively targeted to CHO-hMOR cells showing that DPD-SSL is a drug carrier for the treatment of pain and opioid tolerance.

By modifying dermorphin, a mu opioid ligand, it chemically conjugates to liposomes and helps target the tissue/cells that only express mu opioid receptors.

Methods and compositions disclosed achieve the following:

1) modify dermorphin, a mu opioid ligand, so it can be chemically conjugated to liposome and more stable;

2) target intended tissue/cells that only express mu opioid receptors using modified dermorphin;

3) deliver drugs directly to the intracellular compartment via receptor-mediated interalization; and 4) improve the bioavailability of water-insoluble or non-cell permeable drugs (including peptides) by using sterically-stable liposome construct or polymer device.

Demorphin was conjugated with a commercially available reagent, a PEGylated lipid an embodiment of which is DSPE-PEG(3400)-maleimide, via an addition of cystein at the COOH terminus of the peptide. DSPE-PEG2000 is another embodiment.

Demorphin is a prototype opiate peptide for targeting. Structural analogues of Dermorphin are also suitable. Any of the following peptides can be modified for similar targeting:

DAMGO
enkephalins
endomorphins
dynorphins
endorphins
DPDPE
deltorphin

These approaches will revolutionize the pharmacotherapies for pain, opioid tolerance and opioid addiction. By binding to specific receptors, intracellular events that foster tolerance, are stopped. Lower drug doses may be contemplated, aided also by inhibitors. Basically, the same delivery concept can be used to deliver any cell-permeable or non-permeable compounds (chemicals, peptides, or nucleotides) to an intracellular target. The method is only limited by the available selective inhibitors/antagonists, but not by a compounds' cell/tissue-specificity, or cell permeability. It can also be modified and designed for the targeting of other diseases.

Combining the cell biology knowledge ( receptor mediated internalization) and pharmaceutical methods (liposome, polymer or other carrier systems) to prevent or improve pain and addiction therapies is new.

Sterically stabilized liposomes (SSL) with surface ligands specific for the mu opioid receptor (MOR) actively target MOR-expressing cells. Dermorphin, a selective MOR agonist, was conjugated to $DSPE-PEG_{3400}$ to obtain $DSPE-PEG_{3400}$-dermorphin. Dermorphin-grafted SSL (dermorphin-SSL) was prepared by thin-film rehydration-extrusion and post-insertion method. $DSPE-PEG_{3400}$-dermorphin and dermorphin-SSL retained the affinity to MOR as determined by receptor binding assay using $[^3H]$DAMGO, whereas plain SSL without surface ligands showed no binding to the receptor. Cellular uptake of cholesteryl BODIPY encapsulated dermorphin-SSL was studied. Both fluorescent and confocal microscopy showed that significant fluorescence signal was observed inside CHO-hMOR cells after the treatment with dermorphin-SSL, indicative of MOR-mediated endocytosis. CHO-hMOR cells took up $2.5\times10^4$ dermorphin-SSLs/cell after the treatment, but not plain SSL. In contrast, no uptake of dermorphin-SSL was found in naive CHO cells or CHO-hDOR cells that lack MOR. Taken together, these results demonstrate that a dermorphin-SSL delivery system is capable of targeting intracellular components of MOR-expressing cells. Such a system may be applied to carry pharmaceutical agents to achieve region-specific delivery of analgesics and/or to attenuate side effects associated with opioids.

A method to target an opioid receptor with a pharmaceutical agent includes:

(a) covalently conjugating a modified peptide to a PEGylated lipid to form a conjugate; and (b) inserting the conjugate into a carrier.

The opioid receptor may be a human opioid receptor (hMOR). The carrier may be a nanoparticle (e.g., a sterically stabilized liposome). The conjugate is DPD. The PEGylated lipid is DSPE-PEG3400.

A composition includes:

(a) a peptide;
(b) a carrier, (e.g. liposomes); and
(c) a PEGylated lipid.

A pharmaceutical carrier (delivery) system e.g. dermorphin-SSL includes:

(a) a peptide;
(b) a carrier; and
(c) a PEGylated lipid.

Dermorphin or a suitable substitute is conjugated to sterically stabilized liposomes (SSL) with surface ligands specific to the human mu opioid receptors (hMOR) so it can be actively targeted to the receptor-containing cells, e.g. CHO cells as illustrative embodiments. This is a promising drug carrier for the treatment of pain and opioid tolerance.

BRIEF DESCRIPTION OF THE DRAWINGS

FIG. 1: The size distribution of DPD-SSL by QELS using NICOMP (intensity weighted and volume weighted).

FIG. 2: Standard curve of the modified Bartlet phosphate assay.

FIG. 3. Displacement binding of 3H-DAMGO (1 nM) by dermorphin, c-p-dermorphin and DPD to CHO-hMOR.

FIG. 4: Displacement binding of $^3H$-DAMGO (1 nM) by DPD-SSL to CHO-hMOR.

FIG. 5: DPD-SSL uptake by CHO-hMOR cells (A. CHO-K1 cells, B. CHO-hDOR cells and C. CHO-hMOR cells were incubated with DPD-SSL for 4 h at 37° C.). Cells were viewed by either phase contrast (left images) or fluorescence microscopy (middle images). The right images displayed the blended images of the left and middle. Magnification was X150.

FIG. 6: The synthesis scheme of $DSPE-PEG_{3400}$-dermorphin. The conjugate was synthesized by coupling of the thiol group of modified dermorphin and the maleimide of $DSPE-PEG_{3400}$-MAL. (I) $DSPE-PEG_{3400}$-MAL; (II) modified dermorphin with cysteine residue at C-terminus; (III) $DSPE-PEG_{3400}$-dermorphin.

FIG. 7: Mass spectrum of $DSPE-PEG_{3400}$-dermorphin. The mean molecular weight of $DSPE-PEG_{3400}$-dermorphin was determined to be around 5,200 Da as indicated by the arrow.

FIG. 8: Displacement binding of $[^3H]$DAMGO (1 nM) by dermorphin (■) or $DSPE-PEG_{3400}$-dermorphin (□) to human mu opioid receptors expressed in CHO cells. The specific radioactivity of $[^3H]$DAMGO bound to hMOR in the absence of competing ligands was set to 100%. There was no significant difference between the two groups ($P>0.05$, two-tailed Student's t-test). Each point represents the mean ±S.D. of three experiments (each performed in triplicate).

FIG. 9: Displacement binding of $[^3H]$DAMGO (1 nM) by dermorphin-SSL to CHO-hMOR. Receptor bound $[^3H]$DAMGO was displaced by dermorphin-SSL (■), but not by plain SSL (◇). The specific radioactivity of $[^3H]$DAMGO bound to hMOR in the absence of SSL or dermorphin-SSL was set to 100%. Each point represents the mean ±S.D. of three experiments (each performed in triplicate).

Figure 10:
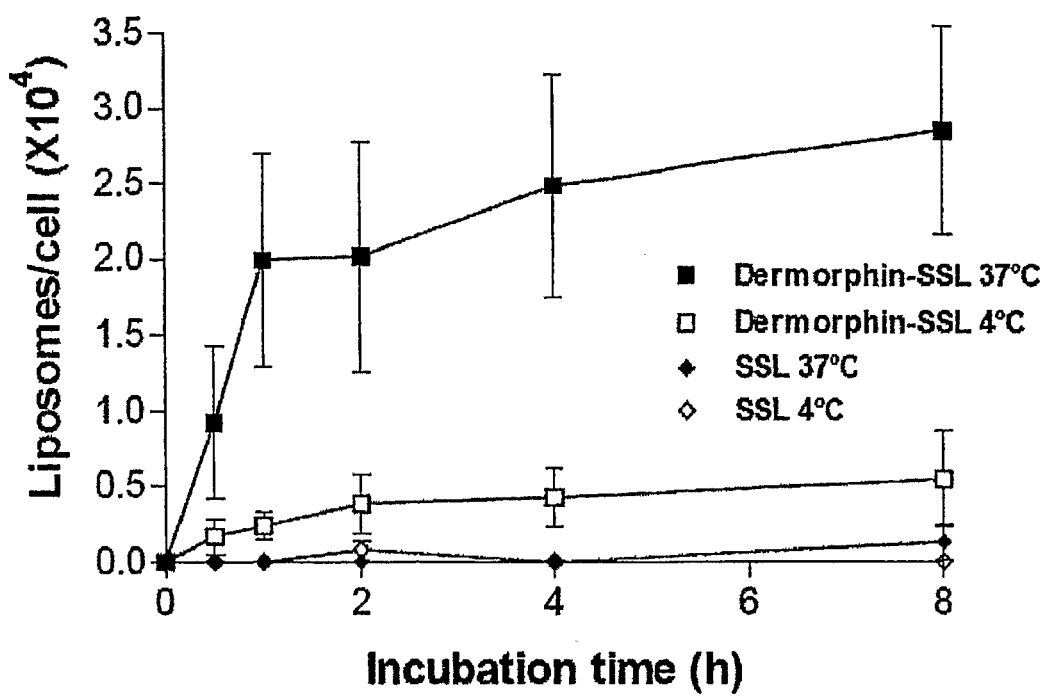

FIG. 10: Time course of dermorphin-SSL and SSL uptake by CHO-hMOR cells. CHO-hMOR cells were incubated with dermorphin-SSL or blank SSL (65 μM phospholipids) at 37° C. or 4° C. for various lengths of time in serum-free growth medium. (■), cells treated with dermorphin-SSL at 37° C.; (□), cells treated with dermorphin-SSL at 4° C.; (◆), cells treated with SSL at 37° C.; (◇), cells treated with SSL at 4° C. Each point represents the mean ±S.D. of two experiments (each performed in triplicate).

Figure 11:
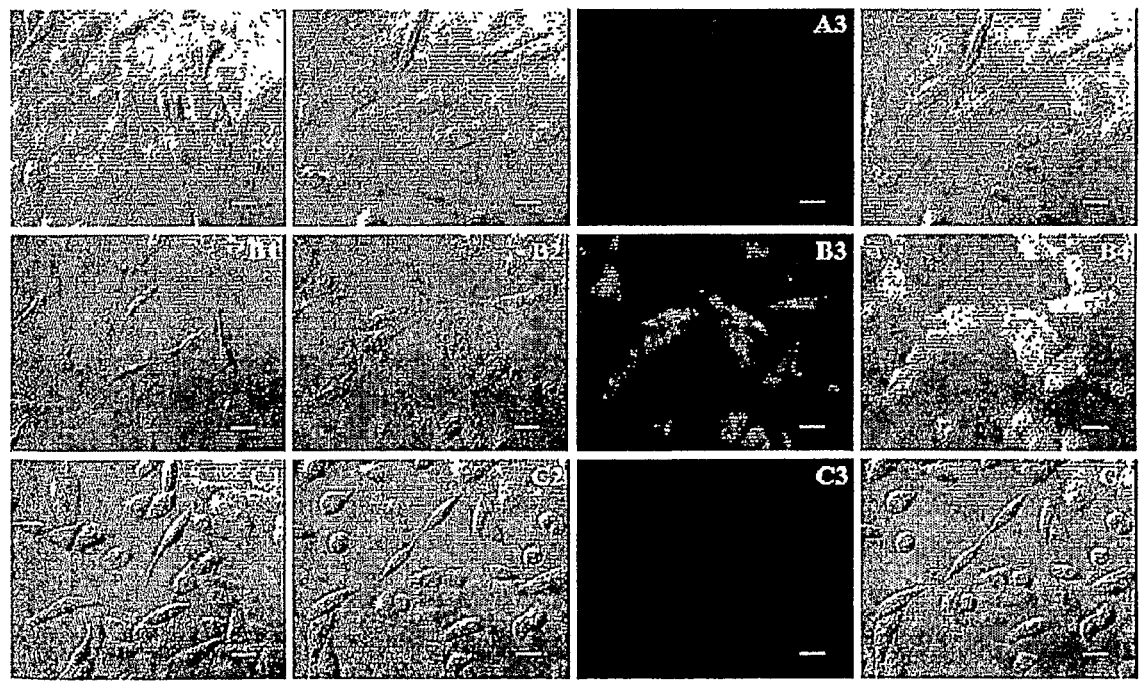

FIG. 11: Internalization of cholesteryl BODIPY encapsulated dermorphin-SSL by CHO-hMOR cells, but not by CHO and CHO-hDOR cells, examined by fluorescent microscopy. CHO (A), CHO-hMOR (B) and CHO-hDOR (C) cells were incubated with dermorphin-SSL (65 μM phospholipids) for 4 h at 37° C. in serum-free growth medium. Cells were fixed with 3.7% paraformaldehyde and viewed by either differential interference contrast (DIC) (A1, B 1, C 1: before dermorphin-SSL treatment; A2, B2, C2: after dermorphin-SSL treatment) or fluorescent microscopy (A3, B3, C3: after dermorphin-SSL treatment). Images of A4, B4 and C4 are the overlay of DIC (A2, B2, C2) and fluorescence (A3, B3, C3), respectively. The absence of fluorescence in CHO and CHO-hDOR cells in contrast to the intense cell-associated fluorescence in CHO-hMOR cells indicated the cell-specific association of dermorphin-SSL. Fluorescent imaging was performed as well in all of the three types of cells treated with plain SSL, but no fluorescence was observed in these cells (figures not shown). Scale bars represent 20 μm.

Figure 12:
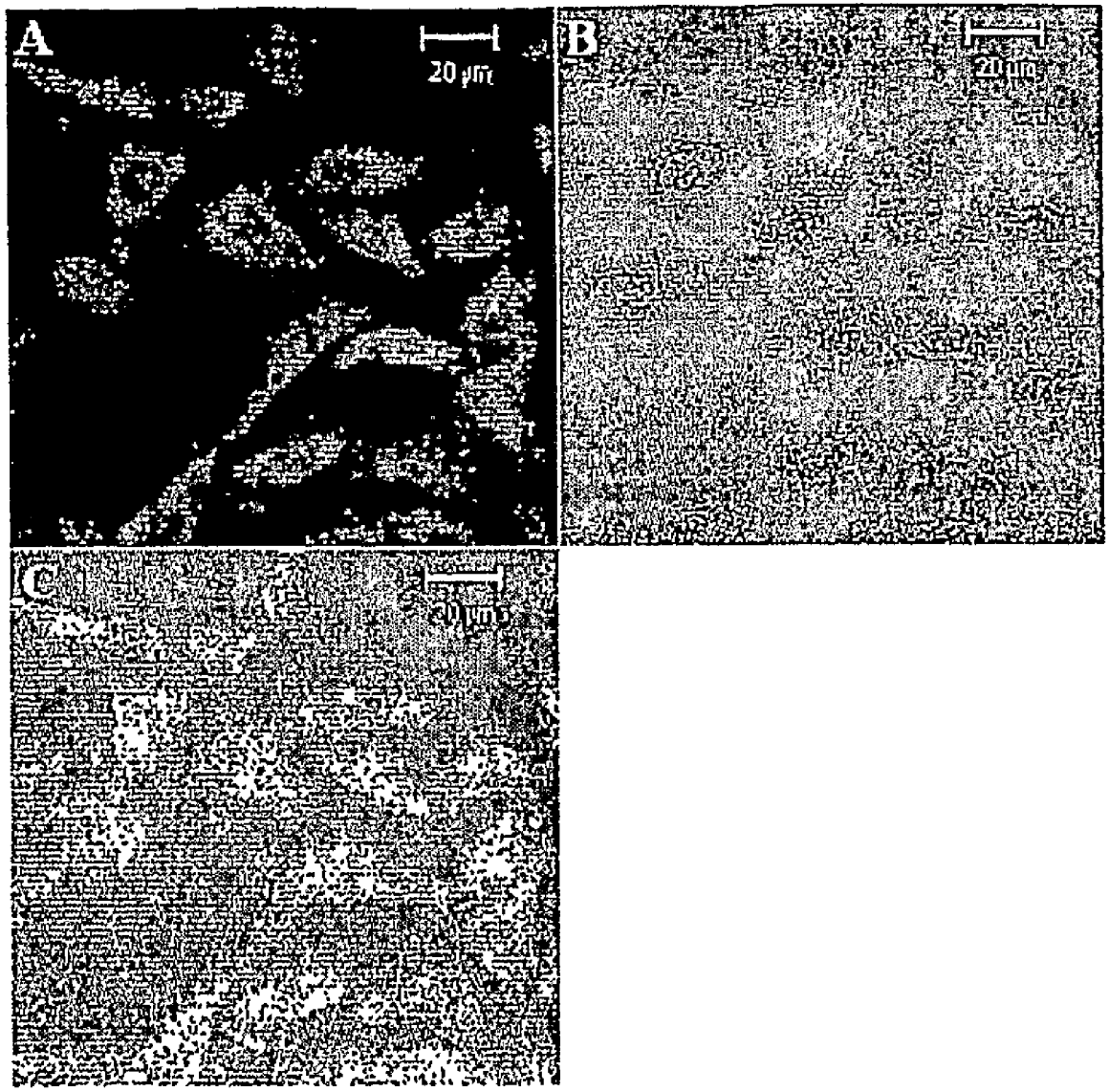

FIG. 12: Confocal image of CHO-hMOR cells after 4 h of incubation with cholesteryl BODIPY encapsulated dermorphin-SSL. (A) Fluorescent image; (B) DIC image; (C) Overlay image of (A) and (B). Scale bars represent 20 μm.

DETAILED DESCRIPTION

Pain, especially that associated with cancer and neuropathy is extremely difficult to treat. Opioids, such as morphine, remain to be most efficacious analgesics. Repeated and prolonged use of these drugs is problematic as tolerance and drug dependence begin to occur, which drastically limits the effectiveness and application of these drugs. Extensive research has been carried out over the past several decades to understand the mechanisms underlying opioid tolerance and dependence. Whereas the exact mechanisms are yet to be completely defined, a number of novel targets, many intracellular, have been identified to attenuate opioid tolerance and dependence (e.g., PKC, CaMKII, CREB). Despite these advances, it is unlikely that these intracellular sites can be reached by conventional delivery methods. Moreover, region-specific intervention is advantageous to achieve specificity and reduce side effects. Developing therapeutically useful agents targeting these novel sites will require target-delivery methods.

Targeted-drug delivery of agents (even peptides or nucleotides) to selected cells to modulate the intended intracellular targets, e.g., the utilization of peptides or ligands coupled to conventional liposomes, is reported. To prolong the circulating half-time of liposomes, a more advanced strategy has been used to apply sterically stabilized liposomes (SSL) with surface ligands to achieve cell-specific targeting. Liposomal delivery systems provide high capacity of drug payload and drug stability, which may become especially beneficial for delivering peptides and nucleotides. Compared with conventional liposomes, SSL has advantages of longer circulating half-life and non-immunogenicity, which can improve the therapeutic efficacy of the encapsulated drugs. Addition of liposome surface ligands provides liposomes with the ability of targeting a specific cell population by recognizing receptors expressed on the targeted cells with high selectivity. Such a method, when in conjunction with receptor-mediated endocytosis, can be particularly powerful to deliver drugs across cytoplasmic membranes.

The mu opioid receptor (MOR), a member of G protein-coupled receptors (GPCR), is primarily responsible for the analgesic and rewarding effects of opioids. Targeting the receptor provides a unique opportunity for improving pain treatment by modulating the analgesic and addictive potential of opioid drugs. Activation of MOR by its agonists such as DAMGO and dermorphin causes internalization of the receptor-ligand complex. In fact, saporin, a cell impermeable cytotoxic agent, has been directly conjugated to dermorphin. Unlike saporin, alone, dermorphin-saporin is capable of entering and killing MOR-expressing cells in rats. It is advisable to eliminate MOR-expressing cells for most clinical therapies. In addition, dermorphin-saporin (1:1) conjugates provides relatively low drug payload.

A dermorphin-grafted SSL system (dermorphin-SSL) to specifically target cells expressing MOR was used. Dermorphin-SSL recognized cell surface MOR and was internalized via MOR-mediated endocytosis, thus it is capable of delivering encapsulated pharmaceutical agents to reach intracellular targets.

Although the exact mechanisms behind opioid tolerance and dependence are not fully understood, a number of intracellular targets such as PKO, CREB and CaMKII have been revealed to play important roles. Therapeutic interventions at these intracellular proteins present unique opportunities to improve opioid analgesia and reduce tolerance and addiction. However, many of these molecules have diverse physiological functions. For instance, PKC is also involved in memory function, hence non-selective delivery of PKC inhibitors may also affect learning and memory. Therefore, a cell-specific delivery system is more desirable in designing therapeutic agents for improving opioid analgesia and minimizing side effects. The mu opioid receptor (MOR) is primarily responsible for the analgesic and rewarding effects of opioids. A dermorphin-grafted sterically stabilized liposome (dermorphin-SSL) has been developed to selectively deliver drugs targeting intracellular components of MOR-expressing cells.

Theoretically any molecule can be directly conjugated to a ligand to achieve targeting delivery to the cells expressing specific receptors; however, ligand-grafted SSL with therapeutic agents encapsulated is suitable for a number of reasons: 1) PEGylated liposomes are sterically stabilized, providing longer circulating half-life and little immunogenicity; 2) liposomes may bear $10^4$ drug molecules, which is several orders of magnitude greater capacity of drug payload than that of ligand-drug conjugate; 3) ligand-grafted liposomes provide a general approach to deliver a number of potential drugs without the need for chemical linkers that must be specifically designed for particular drugs on a case-by-case basis; 4) PEGylated liposomes without surface ligands are not able to target specific cells. Although PEG chains may prolong the circulating half-life of liposomes to a certain extent, a substantial fraction of liposomes will still end up with being taken up by the reticulo-endothelial-system (RES) system and eventually the encapsulated drugs will be released and get into the RES system, which may damage normal cell function and cause significant side effects. PEGylated liposomes with surface ligands can enhance specificity to target cells and only stay confluent in targeted cell areas, which can result in significant changes of the pharmacokinetics and biodistribution of liposomes and incorporated drugs. These properties can decrease RES uptake and reduce negative effects.

Dermorphin is a biologically active opioid heptapeptide that is highly selective and active for MOR. The N-terminal dermorphin tetrapeptide is reported to be the minimal sequence that is required for biological activities. To maintain its high affinity for the receptor, only the C-terminus of dermorphin was modified by adding an additional cysteine residue, so the peptide can be readily conjugated to DSPE-PEG$_{3400}$-MAL to form DSPE-PEG$_{3400}$-dermorphin by coupling of thiol and maleimide groups. The conjugation reaction is highly specific and takes place under mild conditions. The formed thiol-ether bond is not readily hydrolyzed in vivo which confers the stability of DSPE-PEG$_{3400}$-dermorphin. DSPE-PEG$_{3400}$-dermorphin retained affinity and selectivity to MOR (IC50: 1.9 nM), which was not significantly different from that of dermorphin (IC50: 1.6 nM). It appears that N-terminal dermorphin is essential for its affinity to MOR. The mass distribution of DSPE-PEG$_{3400}$-dermorphin shown in mass spectrogram was due to the PEG polymer. The mean molecular weight, determined by MALDI-MS, was 5,200 Da, which was in agreement with the calculated size of DSPE-PEG$_{3400}$-dermorphin.

Dermorphin-SSL was prepared by post-insertion method. It is advantageous that DSPE-PEG can be transferred into the membrane of the preformed liposomes by one-step incubation with very little drug release during the transfer and only small increases in liposome diameters. Moreover, liposomes can be constructed with defined number of targeting ligands that could be controlled by the alteration of incubation time, temperature and ligand concentration.

To study the receptor affinity and cell uptake of dermorphin-SSL, MOR-transfected CHO cells were established. CHO cells do not express endogenous opioid receptors, and they are highly transfectable. Opioid receptors transfected in CHO cells are common models widely employed to study the receptor/ligand interactions, receptor activation, signal transduction, and adaptive changes of these receptors. Receptor activation, phosphorylation, internalization, downregulation, dimerization, and receptor tolerance have all been studied in these cells. CHO cells expressing only a single opioid receptor subtype provides a unique system to study a receptor-selective mechanism. To study the cell-specific uptake of dermorphin-SSL, another cell line expressing the human delta opioid receptors (CHO-hDOR) was employed. Both hMOR and hDOR belong to the family of seven transmembrane G-protein coupled receptors, sharing extensive sequence and structural homologies. Among all known receptors, hDOR is the closest to hMOR; therefore, CHO-hDOR along with untransfected CHO cells were used as controls. Using these receptor-specific cell lines, dermorphin-SSL was only uptaken by CHO-hMOr cells, not CHO or CHO-hDOR cells. It should, however, be noted that these are non-neuronal artificial cell lines that express high levels of receptors.

A 4 h treatment protocol was used to induce significant receptor internalization by a variety of opioid agonists. Moreover, the cell uptake study demonstrated that there was no significant increase of liposome internalization after 4 h. Indeed, cell uptake of dermorphin-SSL only by CHO-hMOR cells was identified, but not by CHO or CHO-hDOR cells. Differential interference contrast (DIC) cell images before and after dermorphin-SSL treatment were taken to demonstrate intact cell morphology, which also indicated low apparent cell toxicity of dermorphin-SSL. Fluorescence signal was observed inside the nuclei of CHO-hMOR cells after the treatment with dermorphin-SSL. This observation may suggest that targeted agents could enter nuclei after the degradation of liposomes, which will be essential to deliver gene (e.g. antisense)-based agents encapsulated in liposomes. For instance, PKC is a major cause of the development of opioid tolerance. Antisense-based agents targeting isoforms of PKC may be incorporated in liposomes to enter nuclei to reach targets. The size of liposomes is another variable that may affect the outcome. It was reported that liposomes with a mean diameter of about 200 nm were not internalized by KB cells. Dermorphin-SSL with a mean diameter of 150 nm were used herein and were internalized by CHO-hMOR cells.

Dermorphin-SSL was capable of specifically recognizing the cell surface MOR, and leading to MOR-mediated endocytosis of liposomes in vitro. Dermorphin-SSL can be intrathecally delivered to animal spinal cord, thus bypassing the blood brain barrier and directly introducing liposomes to spinal cord cells.

DPD-SSL Preparation and Characterization

Figure 2:
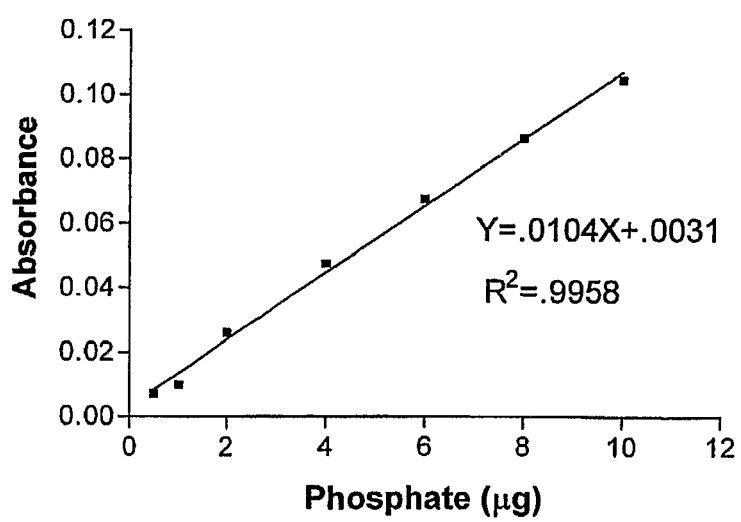

The size of DPD-SSL was around 98 nm and the distribution was shown in FIG. 1. The phospholipid concentration was 6.32 mM after gel filtration (FIG. 2. standard curve). The number of DPD molecules per liposome was about 50 per liposome.

Receptor Binding Experiment

Figure 3:
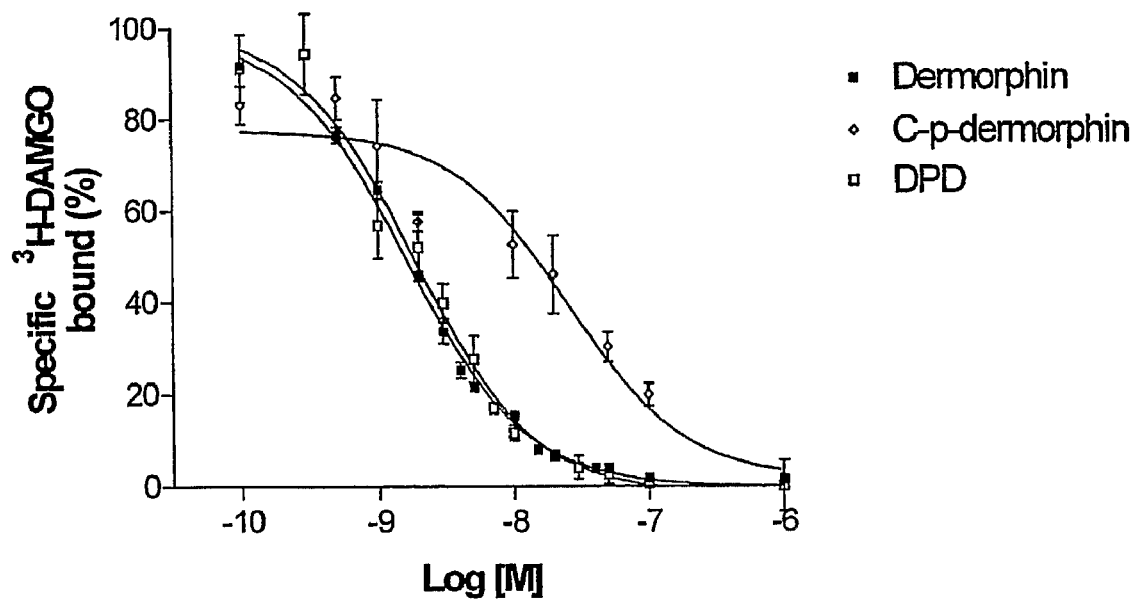

As shown in FIG. 3, DPD completely displaced the binding of 3H-DAMGO to CHO-hMOR at the highest concentration of 8 μM as well as dermorphin. The IC50 values of DPD and dermorphin were 1.9 nM and 1.6 nM, respectively, which indicated no significant difference (p>0.05) between the binding affinities of DPD and dermorphin to MOR. It demonstrated that the DPD conjugate does not affect the affinity of dermorphin to MOR. The modified dermorphin intermediate, c-p-dermorphin, showed decreased MOR binding affinity (IC50=25.3 nM), which might be due to its impurity.

Figure 4:
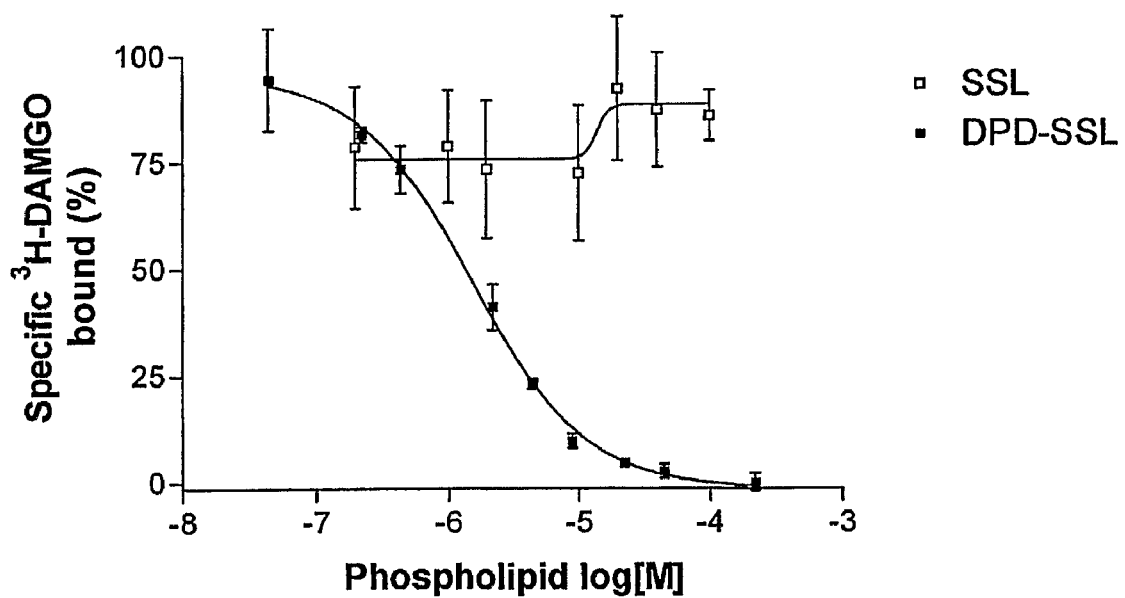

As shown in FIG. 4, DPD-SSL also completely displaced the binding of 3H-DAMGO to CHO-hMOR as the phospholipid concentration went up to 0.2 mM. The IC50 of DPD-SSL was 1.5 μM. However, SSL was not able to displace the binding of 3H-DAMGO to CHO-hMOR. This demonstrated that only DPD-SSL which was ligand-grafted was able to specifically bind to MOR.

Cellular Uptake of DPD-SSL

Figure 5:
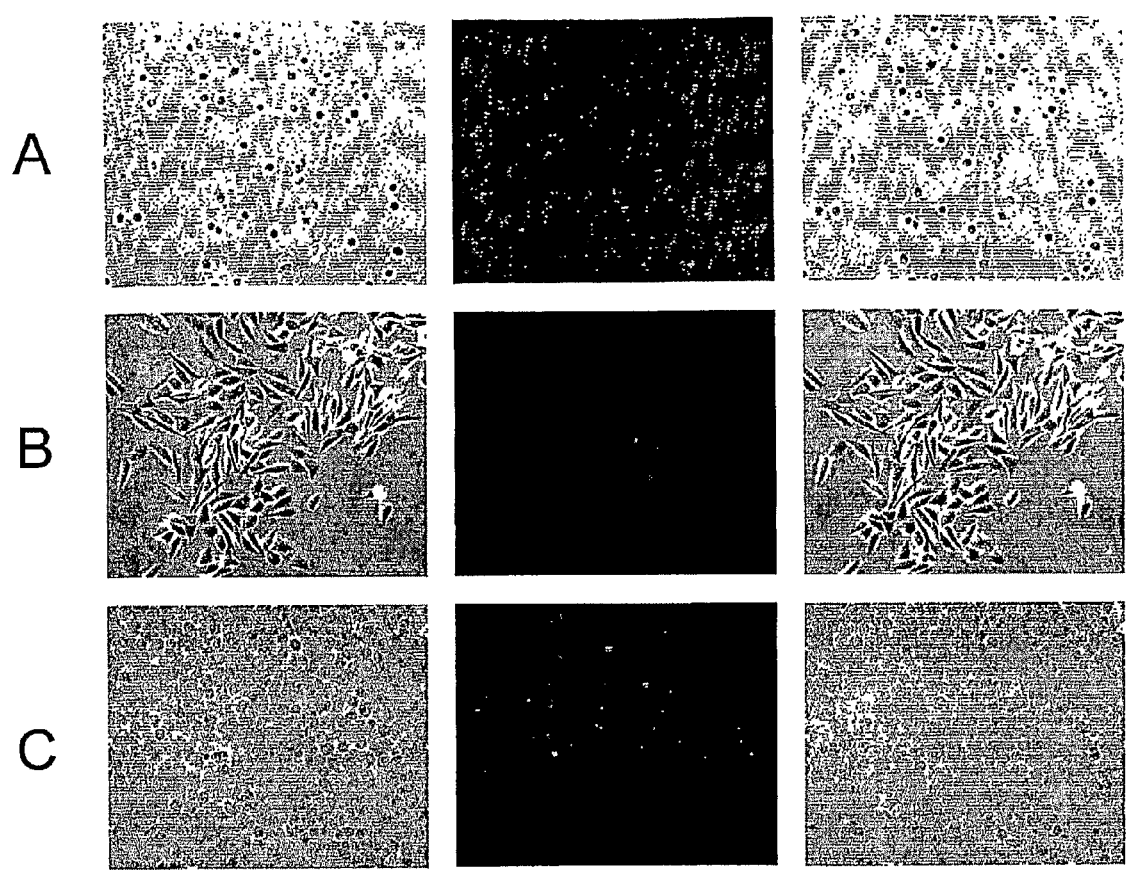

CHO cells are well known models for mammalian cells. By 4 h of incubation with DPD-SSL, the cytoplasm of CHO-hMOR cells showed significant fluorescence that indicated the uptake of DPD-SSLs by CHO-hMOR cells. However, the fluorescent signal was not found inside of CHO-hDOR and CHO-K1 cells. This demonstrated that DPD-SSL was capable of recognizing specifically the cell surface MOR and leading to MOR-mediated endocytosis of DPD-SSL. (FIG. 5)

Conjugation of Dermorphin to DSPE-PEG

A modified dermorphin peptide (Tyr-d-Ala-Phe-Gly-Tyr-Pro-Ser-Cys) was synthesized by the Fmos solid state peptide synthesis method using a Symphony peptide synthesizer (Protein Technologies, Tucson, Ariz.). The product was purified on a reversed-phase Vydac 218TP1010 C 18 column (Hesperia, Calif.) using a HP 1100 HPLC system (Agilent Technologies, Wilmington, Del.). A flow rate of 5 ml/min using solvent A (0.1% TFA in Mili-Q water) and solvent B (0.1% TFA in acetonitrile) was used. The column was equilibrated with 5% solvent B. After sample injection, the column was eluted with a linear gradient from 5% solvent B to 100% solvent B in 60 min. Cyano-4-hydroxycinnamic acid (CHCA) was used as the matrix for mass spectrometric analysis of the peptide product. Samples were mixed 1:1 with the matrix solution (10 mg CHCA in 1 ml aqueous solution of 50% acetonitrile containing 0.1% TFA). Aliquots (1.3 ul) were spotted onto a matrix-assisted laser desorption/ionization time-of-flight (MALDI-TOF) target and analyzed by a Voyager-DE PRO Mass Spectrometer (Applied Biosystems, Foster City, Calif.) equipped with a 337 nm pulsed nitrogen laser. The verified peptide was conjugated to an activated DSPE-PEG (DSPE-PEG3400-Maleimide, Avanti, Alabaster, Ala.), in a molar ratio of 1:10. The reaction was carried in PBS containing 5 mM EDTA overnight in room temperature. The conjugation was purified by HPLC and structurally verified by mass spectrometry as described herein. The masses of the peptide and peptide-DSPE-PEG conjugate were measured using a positive-ion linear mode over the m/z 1000-6500. External mass calibration was performed using peaks of a mixture of bradykinin fragments 1-7 at 757 Da, angiotensin II (human) at 1046 Da, $P_{14}R$ (synthetic peptide) at 1533 Da, adrenocorticotropic hormone fragment 18-39 (human) at 2465 Da, insulin oxidized B (bovine) at 3494 Da, and insulin (bovine) at 5735 Da.

EXAMPLE 1

MOR-Mediated Endocytosis of DPD-SSL

Dermorphin, a selective MOR agonist, was covalently conjugated to DSPE-PEG3400-MAL (MW 3400) to obtain the conjugate of DSPE-PEG3400-dermorphin (DPD). DPD was then inserted into preformed sterically stabilized liposomes (SSL). The affinity of DPD-SSL to mu opioid MOR was evaluated by a receptor binding assay using known MOR agonist as a control. To study the uptake of DPD-SSL, cholesteryl BODIPY was incorporated in the membrane of DPD-SSL. The internalization of DPD-SSL was studied by fluorescence microscopy in cultured CHO cells stably expressing opioid mu and delta receptors.

The results demonstrated that DPD-SSL was capable of recognizing specifically the cell surface MOR and leading to MOR-mediated endocytosis of DPD-SSL. Such delivery system may be useful for carrying agents that can directly attenuate chronic pain or potentiate opioid-analgesia.

The structures of dermorphin, DSPE-PEG, and DPD conjugate were confirmed by Mass Spectrometry. DPD-SSL demonstrated high specific affinity to MOR, completely inhibiting DAMGO binding to CHO-MOR. Blank SSL showed no binding to the receptor. Significant fluorescence was observed inside CHO-hMOR cells, indicative of MOR-mediated internalization after the treatment with DPD-SSL, but not SSL (both contained cholesteryl BODIPY).

These results demonstrated that DPD-SSL was capable of recognizing specifically the cell surface MOR and leading to MOR-mediated endocytosis of DPD-SSL. Such delivery system will be useful for carrying agents that can directly attenuate chronic pain or potentiate opioid-analgesia.

EXAMPLE 2

Synthesis of DSPE-PEG$_{3400}$-dermorphin

Figure 6:
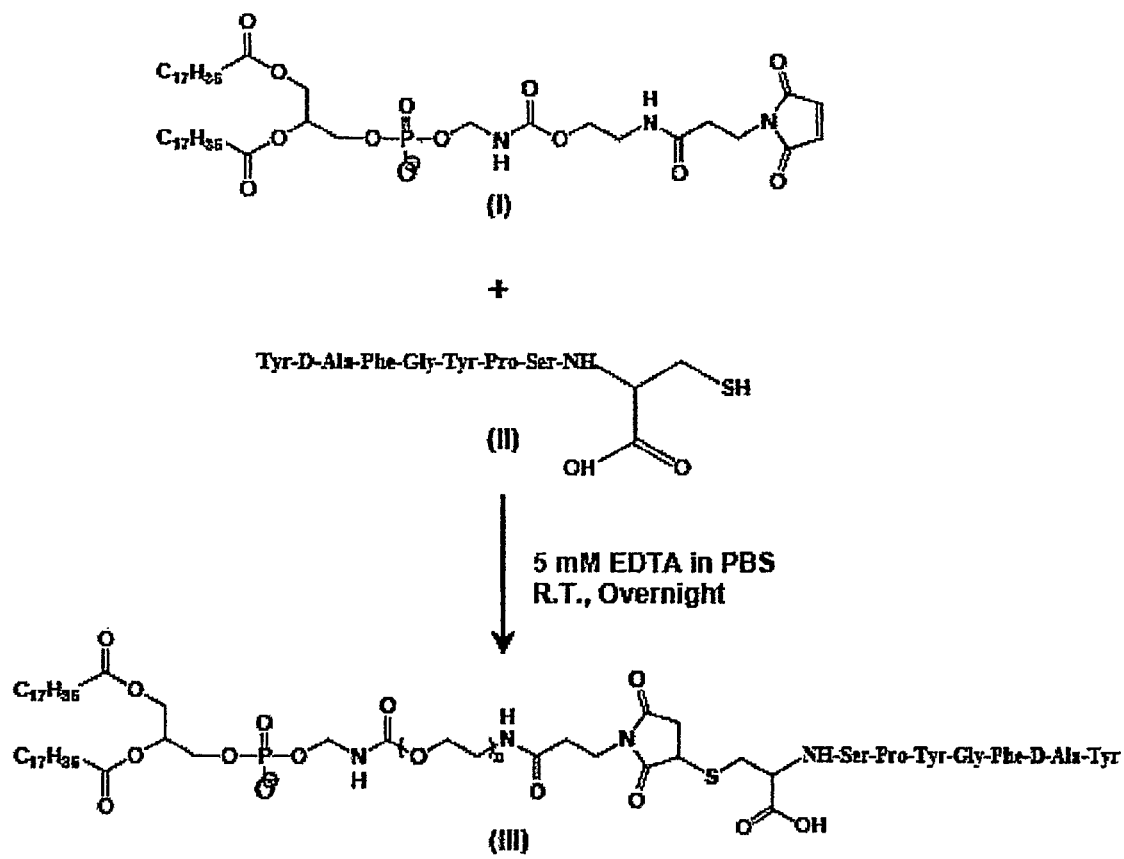
Figure 7:
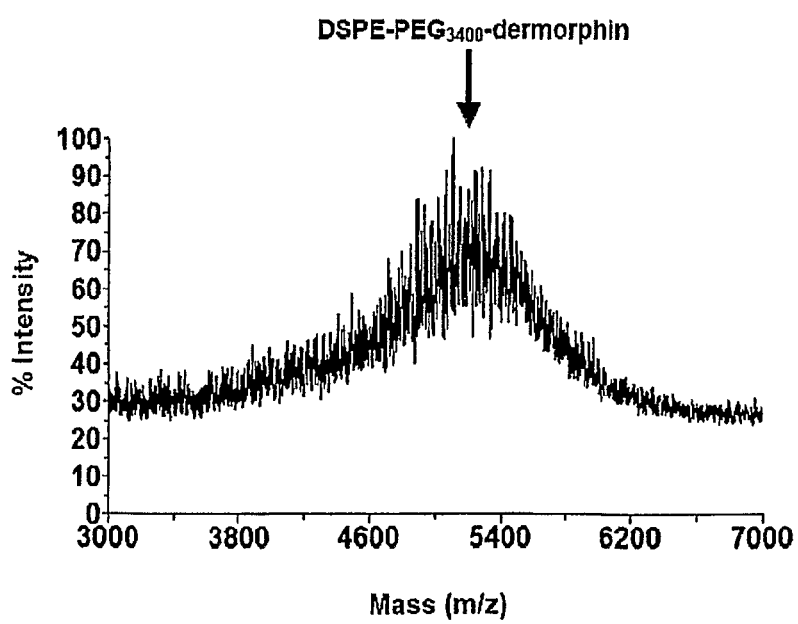

DSPE-PEG$_{3400}$-dermorphin was synthesized by a single step reaction of DSPE-PEG$_{3400}$-MAL with modified dermorphin peptide (Tyr-D-Ala-Phe-Gly-Tyr-Pro-Ser-Cys) as shown in FIG. 6. The reaction was carried out at room temperature overnight in phosphate buffered saline containing 5 mM EDTA. DSPE-PEG$_{3400}$-dermorphin was purified by HPLC and structurally confirmed by mass spectrometry. The peak at 5,200 mass-charge ratio at a charge of 1 verified that the mean molecular weight of DSPE-PEG$_{3400}$-dermorphin was 5,200 Da (FIG. 7), which was in agreement with the calculated molecular weight of the conjugate. Amino acid analysis confirmed the amino acid composition of the modified dermorphin and DSPE-PEG$_{3400}$-dermorphin. The final conjugation yield for the coupling reaction between DSPE-PEG$_{3400}$-MAL and the modified dermorphin was over 90%.

EXAMPLE 3

Affinity of DSPE-PEG$_{3400}$-dermorphin to MOR

Figure 8:
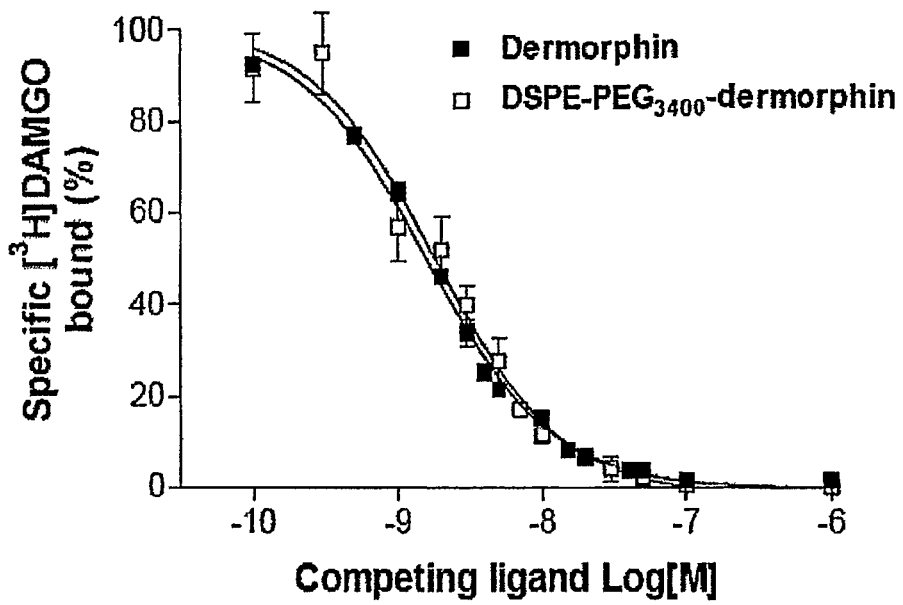

The affinities of dermorphin and DSPE-PEG$_{3400}$-dermorphin were determined in CHO-hMOR cells by radioligand receptor binding assay. Dermorphin and DSPE-PEG$_{3400}$-dermorphin showed identical binding property and their displacement curves were nearly superimposed. Both dermorphin and DSPE-PEG$_{3400}$-dermorphin completely displaced the binding of [$^3$H]DAMGO, a selective MOR agonist, to hMOR (FIG. 8). The IC50 values were determined to be 1.9±0.6 nM and 1.6±0.3 nM (S.D.) for DSPE-PEG$_{3400}$-dermorphin and dermorphin, respectively (not statistically different). These data indicated that DSPE-PEG modification of dermorphin did not alter its affinity to hMOR.

EXAMPLE 4

Characterization of dermorphin-SSL

After determining the retained affinity of DSPE-PEG$_{3400}$-dermorphin to MOR, DSPE-PEG$_{3400}$-dermorphin was micellized and incubated with preformed SSL to prepare dermorphin-grafted SSL as described in Materials and Methods. The mean diameter of dermorphin-SSL was determined to be 150±30 nm (S.D.) by the analysis of volume- or intensity-weighted distribution using NICOMP. The size of dermorphin-SSL exhibited the Gaussian distribution. Following gel filtration to remove DSPE-PEG$_{3400}$-dermorphin unincorporated into the phospholipid bilayer of SSL, the phospholipid content of dermorphin-SSL was determined to be 4.44 mM by the modified Bartlett phosphate assay and the number of dermorphin molecules per liposome was calculated to be around 250.

EXAMPLE 5

Affinity of dermorphin-SSL to MOR

Figure 9:
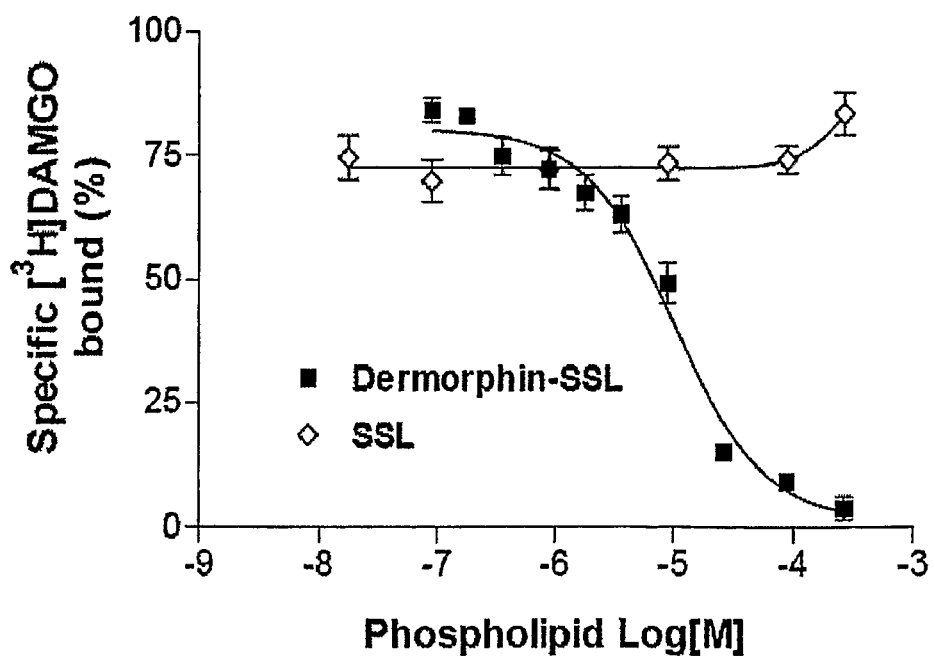

In order to determine whether dermorphin-SSL could still bind to the mu opioid receptor, a series of different concentrations of dermorphin-SSL were used to complete the binding of [$^3$H]DAMGO to CHO-hMOR (FIG. 9). At high concentrations, dermorphin-SSL completely displaced the [$^3$H] DAMGO binding, indicating that dermorphin-SSL retained its receptor affinity. In contrast, plain SSL without surface ligands was not able to complete the binding of [$^3$H]DAMGO to CHO-hMOR (FIG. 9). Therefore, only dermorphin-grafted liposomes were able to recognize and bind to MOR.

EXAMPLE 6

Cellular Uptake of dermorphin-SSL

The results of cell uptake study are shown in FIG. 10. To study the kinetics of liposome uptake by MOR-expressing cells, CHO-hMOR cells were incubated with fluorescent dermorphin-SSL or SSL containing 65 μM phospholipids for various intervals. To distinguish cell membrane-bound from internalized liposomes, CHO-hMOR cells were incubated at either 4° C. or 37° C. and then rinsed with ice-cold PBS to remove free liposomes. At 37° C., the uptake of dermorphin-SSL (including membrane-bound and internalized) increased dramatically over the first hour of incubation in a linear manner and then slowly over the next seven hours. In contrast, the uptake of dermorphin-SSL (only membrane-bound) at 4° C. was much lower. This suggests that the substantial fraction of liposome uptake was due to the internalization. At 4 h and 8 h, the cell uptake was $2.5 \times 10^4$ and $2.8 \times 10^4$ liposomes/cell, of which about 83% and 81% was obtained due to the internalization of liposomes, respectively. However, there was no or little cell uptake occurred for plain SSL at either temperature. Therefore, only dermorphin-SSL bound to MOR and was able to be taken up by CHO-hMOR cells.

EXAMPLE 7

Fluorescent Imaging

To test the receptor-mediated cell uptake of liposomes, CHO, CHO-hMOR and CHO-hDOR cells were incubated with dermorphin-SSL or plain SSL for 4 h at 37° C. In these experiments, cholesteryl BODIPY was encapsulated in liposomes for two purposes: 1) to simulate encapsulation of a chemical compound in our system; 2) to monitor the whereabouts of liposomes by fluorescent signals. To avoid nonspecific adhesion, cells were washed extensively with phosphate-buffered saline. Significant fluorescent signals were observed in CHO-hMOR cells after the treatment with dermorphin-SSL for 4 h (FIG. 11). In contrast, no fluorescence signal was observed in either CHO-hDOR or CHO cells after the treatment with dermorphin-SSL (FIG. 11). Moreover, no fluorescence was detected after the treatment of CHO, CHO-hMOR and CHO-hDOR cells with plain SSL. After 4 h incubation with liposomes, no significant cell morphology changes were observed for all three types of CHO cells, suggesting little apparent cell toxicity of dermorphin-SSL.

To exclude the possibility that dermorphin-SSL is simply associated with the outer cell surface, but does not get internalized by cells, dermorphin-SSL treated CHO-hMOR cells were examined using confocal laser microscopy by scanning the confocal plane every 400 nm. Indeed, intense fluorescence signal was detected inside cells, indicating cellular uptake of dermorphin-SSL (FIG. 12). These results suggested that dermorphin-SSL was capable of recognizing MOR and being internalized into CHO-hMOR cells with the encapsulated fluorescent probe. Therefore, a dermorphin-SSL system is suitable and capable of carrying drugs to intracellular components of intended (targeted) cells.

Materials and Methods

Dermorphin, a selective MOR agonist, was covalently conjugated to DSPE-PEG3400-MAL (MW 3400) to obtain the conjugate of DSPE-PEG3400-dermorphin (DPD). DPD was then inserted into preformed SSL. The affinity of DPD-SSL to MOR was evaluated by a receptor binding assay using known MOR agonist as a control. To study the uptake of DPD-SSL, cholesteryl BODIPY was incorporated in the membrane of DPD-SSL. The internalization of DPD-SSL was studied by fluorescence microscopy in cultured CHO cells stably expressing opioid mu and delta receptors.

DPD-SSL Preparation and Characterization

Egg PC, DPPG, DSPE-PEG2000, and cholesterol were dissolved in the mixture of chloroform and methanol (9:1 v/v) at the molar ratios of 0.50:0.10:0.03:0.35 and dried to a thin film in a round bottom flask by using a rotary evaporator at 45° C., 90 rpm, 600 mm Hg pressure under Argon. For fluorescent DPD-SSL preparation, a non-exchangeable fluorescent probe, cholesteryl BODIPY, was incorporated in the lipid mixture at 1:1500 molar ratio (lipid:probe). Complete dryness was achieved by desiccation under vacuum overnight. The dry lipid film was hydrated in 0.01 M isotonic HEPES buffer (pH 7.4) and then votexed and sonicated. The formed SSLs were extruded 13 times through a 100 nm pore size polycarbonate filter at first and then 15 times through a 50 nm pore size polycarbonate filter using a Liposofast extruder (Avestin). DPDs were dissolved in pH 6.8 HEPES buffer and incubated with preformed SSLs for about 3 h at 37° C. in a water bath. The free DPDs were then removed by passing the liposomes suspension down an EconPac 10 DG desalting column and DPD-SSL fraction was collected.

The size distribution of DPD-SSLs was determined by quasi-elastic light scattering using a NICOMP Particle Sizer Model 370 (Particle Sizing Systems). The phospholipid content of SSLs was determined by the modified Bartlet phosphate assay). The total amount of DPD and the number of DPD molecules per liposome was determined by comparison of the displacement percentage of DPD-SSL to a standard curve of competitive mu opioid receptor (MOR) binding of DPD and the known phospholipid concentration.

Receptor Binding Experiment

Receptor membranes were prepared from CHO cells transfected with opioid mu receptors. Binding was performed at 30° C. in 50 mM pH 7.4 tris HCl buffer for 1 h for CHO-MOR (100 μg protein/reaction, 1 nM 3H-DAMGO). Reactions were terminated by vacuum filtration through GF/B filters pretreated with 0.2% polyethylenimine. These were then washed twice with ice-cold PBS. Filter-bound radioactivity was determined by liquid scintillation counting. Nonspecific binding was determined in the presence of 20 μM DAMGO.

Cellular Uptake of DPD-SSL

CHO-hMOR, CHO-hDOR and CHO-K1 cells were grown in Dulbecco's modified Eagle's medium and Hank's F12 (1:1 v/v) supplemented with 10% (v/v) newborn calf serum. For CHO-hMOR and CHO-hDOR cells, the media contained 200 μg/ml G418 and hygromycin B, respectively. For cellular uptake experiment, cells (2×104) were plated on coverslips on 24-well culture dishes and cultured overnight. The media were changed to Opti-MEM with 20 mM HEPES before the addition of DPD-SSL. After incubation with DPD-SSL at 37° C. for 4 h, cells were rinsed 3 times with PBS and examined under a fluorescence microscope.

Materials

Egg-phosphatidylcholine (PC), cholesterol (CH), polyethylenimine (PEI) and bovine serum albumin were purchased from Sigma (St. Louis, Mo.). Dipalmitoyl phosphatidyl-glycerol (DPPG) was from Sygena (Switzerland). 1,2-distearoylglycero-3-phosphoethanolamine-N-[poly(ethylene glycol) 2000] ($DSPE-PEG_{2000}$) was obtained from Shearwater Polymers Inc. (Huntsville, AL). $DSPE-PEG_{3400}$-maleimide ($DSPE-PEG_{3400}$-MAL) was purchased from Avanti Polar Lipids (Alabaster, Ala.). Cholesteryl BODIPY (fluorescent probe) was from Molecular Probes Inc. (Portland, Oreg.). Dermorphin, DAMGO ([D-Ala2,N-Me-Phe4,Gly5-ol]-enkephalin) and [$^3$H]DAMGO were provided by Multiple Peptide Systems (San Diego, Calif.). Dulbecco's modified eagle medium, Ham's F-12, penicillin and streptomycin, G418 and hygromycin B were from Cellgro (Herndon, Va.). Newborn calf serum was from BioWhittaker Inc. (Walkersville, Md.

Cell Culture

Chinese hamster ovary cells (CHO, ATCC, Manassas, Va. CHO cells stably transfected with human mu opioid receptors (CHO-hMOR) [26,27], and CHO cells stably transfected with human delta opioid receptors (CHO-hDOR) [28,29] were cultured in 1:1 Dulbecco's modified eagle medium (DMEM) and Ham's F-12 supplemented with 10% newborn calf serum, 100 IU/ml penicillin and 100 μg/ml streptomycin. To maintain stable selection, 200 μg/ml G418 or hygromycin B was added to CHO-hMOR or CHO-hDOR cells, respectively. Cells were cultured in incubators maintained at 37° C. with 5% $CO_2$ in humidified air.

Synthesis of DSPE-$PEG_{3400}$-dermorphin

First a modified dermorphin peptide (Tyr-D-Ala-Phe-Gly-Tyr-Pro-Ser-Cys) was synthesized by the Fmos solid-state peptide synthesis method using a Symphony peptide synthesizer (Protein Technologies, Tucson, Ariz.). The crude peptide was purified on a reversed-phase Vydac 218TP1010 C18 column (Hesperia, Calif.) using a HP1100 HPLC system (Agilent Technologies, Wilmington, Del.). A flow rate of 5 ml/min using solvent A (0.1% TFA in Milli-Q water) and solvent B (0.1% TFA in acetonitrile) was used. The column was equilibrated with 5% solvent B. After sample injection, the column was eluted with a linear gradient from 5% solvent B to 100% solvent B in 60 min. The pure peptide fraction was identified by a matrix-assisted laser desorption/ionization time-of-flight (MALDI-TOF) mass spectrometer. Cyano-4-hydroxycinnamic acid (CHCA) was used as the matrix for mass spectrometric analysis of the peptide product. Samples were mixed 1:1 with the matrix solution (10 mg CHCA in 1 ml aqueous solution of 50% acetonitrile containing 0.1% TFA). Aliquots (1.3 μl) were spotted onto a MALDI-TOF target plate and analyzed by a Voyager-DE PRO Mass Spectrometer (Applied Biosystems, Foster City, Calif.) equipped with a 337 nm pulsed nitrogen laser. The verified peptide was conjugated at room temperature overnight to the activated DSPE-PEG (DSPE-$PEG_{3400}$-MAL), at a molar ratio of 1:10 in PBS containing 5 mM EDTA. The conjugate was purified by HPLC and structurally verified by mass spectrometry using the above protocol. The masses of the peptide and DSPE-$PEG_{3400}$-dermorphin conjugate were measured using a positive-ion linear mode over the m/z 1000-6500. External mass calibration was performed using peaks of a mixture of bradykinin fragments 1-7 at 757 Da, angiotensin II (human) at 1,046 Da, P14R (synthetic peptide) at 1,533 Da, adrenocorticotropic hormone fragment 18-39 (human) at 2,465 Da, insulin oxidized B (bovine) at 3,494 Da, and insulin (bovine) at 5,735 Da.

Preparation of Dermorphin-SSL

Dermorphin-SSL was prepared by thin-film rehydration-extrusion and post-insertion method described previously [16,30,31]. Briefly, egg PC, DPPG, DSPE-$PEG_{2000}$, and cholesterol were dissolved in the mixture of chloroform and methanol (9:1 v/v) at the molar ratios of 0.50:0.10:0.03:0.35 and dried to a thin film in a round bottom flask using a rotary evaporator at 45° C., 90 rpm, 600 mm Hg pressure under Argon. For fluorescent dermorphin-SSL preparation, a non-exchangeable fluorescent probe, cholesteryl BODIPY, was incorporated in the lipid mixture at 1:1500 molar ratio (probe: lipid). Complete dryness was achieved by desiccation under vacuum overnight. The dry lipid film was hydrated in 0.01 M isotonic HEPES buffer (pH 7.4) and then vortexed and sonicated. The formed SSL was extruded through a 100 nm pore size polycarbonate filter using a Liposofast extruder (Avestin, Canada). DSPE-$PEG_{3400}$-dermorphin was dissolved in pH 6.6 HEPES buffer and then inserted into preformed SSL by incubation for 3 h at 37° C. to obtain dermorphin-SSL. Free DSPE-$PEG_{3400}$-dermorphin was removed by passing SSL through an EconPac 10DG desalting column (Bio-Rad, Hercules, Calif.).

Characterization of Dermorphin-SSL

The size of dermorphin-SSL was determined by quasi-elastic light scattering (QELS) method using a NICOMP Particle Sizer Model 370 (Particle Sizing Systems, Santa Barbara, Calif.). The phospholipid content of dermorphin-SSL was measured by the modified Bartlett phosphate assay [32]. The concentration of DSPE-$PEG_{3400}$-dermorphin in liposomes was determined by receptor binding assay using [$^3$H]DAMGO. The number of dermorphin molecules per liposome was then determined as DSPE-$PEG_{3400}$-dermorphin concentration divided by liposome concentration that was estimated according to the relationship between the known phospholipid concentration and liposome size [33].

In vitro Receptor Binding Assay

Receptor binding assay was performed based on the method previously described. Briefly, membranes were prepared from CHO-hMOR cells by Polytron homogenization at setting 6 for 2 min on ice, followed by centrifugation at 20,000 g for 30 min at 4° C. Protein content was determined by the Coomassie protein assay method (Pierce Biotechnology, Rockford, Ill.) and bovine serum albumin as the standard. MOR receptor binding was conducted in triplicate with 1 nM [$^3$H]DAMGO in 50 mM Tris HCl buffer (pH 7.4) at 30° C. for 1 h (50 μg protein/reaction). Nonspecific binding was determined in the presence of 20 μM unlabelled DAMGO. Reactions were terminated by rapid vacuum filtration through GF/B filters presoaked with 0.2% polyethylenimine. Filter-bound radioactivity was determined by liquid scintillation counting (Beckman Coulter Inc., Fullerton, Calif.). Binding data representing the mean ±SD were analyzed using Prism program (GraphPad Software, San Diego, Calif.).

Cellular Uptake of Dermorphin-SSL

CHO-hMOR cells were plated in 24-well cell culture dishes at an initial density of 200,000 cells/well and grown for 24 h under the condition described above. Before the experiments, cell monolayers were rinsed with serum-free growth medium for 3 times. Serum-free medium (0.5 ml/well) containing fluorescent dermorphin-SSL or SSL (final phospholipid concentration: 65 μM) was added to each well. The cells were incubated for 0, 0.5, 1, 2, 4 and 8 h at 37° C. or 4° C. The total cell uptake was estimated at the end of incubation, the medium was removed, and the cells were washed three times with ice-cold PBS, before the cells were scraped off and lysed in the lysis buffer (1% triton X-100 in PBS). The lysate was vortexed and then centrifuged at 20,000 g for 15 min at 4° C. The supernatant was collected and measured for fluorescence intensity using a SpectraMAX Gemini XS microplate spectrofluorometer (Molecular Devices, Sunnyvale, Calif.). To convert the fluorescence intensity to the number of liposomes, a standard curve was constructed by measuring the fluorescence intensity of cell-lysis buffer containing different concentrations of known numbers of liposomes.

Fluorescent Imaging

CHO, CHO-hMOR and CHO-hDOR cells were seeded onto the 12-mm diameter circle coverslips precoated with 0.2% gelatin at a density of 50,000 cells/well and cultured 24 h before the experiment. To study receptor-mediated dermorphin-SSL uptake, cells were treated with fluorescent dermorphin-SSL (65 μM phospholipids) in serum-free growth medium for 4 h. Then cells were rinsed three times with phosphate-buffered saline and fixed with 3.7% paraformaldehyde for 10 min. Thereafter, coverslips containing cells were washed three times with phosphate-buffered saline and once more with deionized water. Coverslips were mounted onto slides using fluorescence mounting medium (Vector Laboratories, Inc., Burlingame, Calif.) and examined for fluorescent signals using Olympus IX70 inverted fluorescence microscope (Olympus Corp., Lake Success, N.Y.) and Carl Zeiss Laser Scanning System 510 (Carl Zeiss MicroImaging, Thornwood, N.Y.) [34].

PUBLICATIONS CITED

These publications are incorporated by reference to the extent they further describe materials and compositions disclosed herein.

[1] K. O. Aley, J. D. Levine, J Neurosci 17 (1997) 8018-8023.
[2] F. L. Smith, et al., Brain Res 985 (2003) 78-88.
[3] Z. J. Wang, L. Tang, L. Xin, Eur J Pharmacol 465 (2003) 199-200.
[4] Z. Wang, W. Sadee, Eur J Pharmacol 389 (2000) 165-171.
[5] G. H. Fan, et al., Mol Pharmacol 56 (1999) 39-45.
[6] R. Maldonado, et al., Science 273 (1996) 657-659.
[7] A. S. Leonard, J. W. Hell, J Biol Chem 272 (1997) 12107-12115.
[8] V. Weissig, et al., FEBS Lett 202 (1986) 86-90.
[9] R. M. Straubinger, et al., Cancer Res 48 (1988) 5237-5245.
[10] K. K. Matthay, et al., Cancer Res 49 (1989) 4879-4886.
[11] B. J. Hughes, et al., Cancer Res 49 (1989) 6214-6220.
[12] J. P. Leonetti, et al., Proc Natl Acad Sci U S A 87 (1990) 2448-2451.
[13] A. Mori, et al., Pharm Res 10 (1993) 507-514.
[14] R. J. Lee-P. S. Low, J Biol Chem 269 (1994) 3198-3204.
[15] J. W. Park, et al., Proc Natl Acad Sci U S A 92 (1995) 1327-1331.
[16] S. Dagar, et al., J Control Release 74 (2001) 129-134.
[17] R. E. Eliaz, F. C. Szoka, Jr., Cancer Res 61 (2001) 2592-2601.
[18] E. Mastrobattista, et al., J Biol Chem 277 (2002) 27135-27143.
[19] C. Mamot, et al., Cancer Res 63 (2003) 3154-3161.
[20] I. Sora, et al., Proc Natl Acad Sci U S A 94 (1997) 1544-1549.
[21] H. W. Maffhes, et al., Nature 383 (1996) 819-823.
[22] G. Gaudriault, et al., J Biol Chem 272 (1997) 2880-2888.
[23] J. R. Arden, et al., J Neurochem 65 (1995) 1636-1645.
[24] V. A. Alvarez, et al., J Neurosci 22 (2002) 5769-5776.
[25] F. Porreca, et al., J Neurosci 21 (2001) 5281-5288.
[26] N. Zaveri, et al., Eur J Pharmacol 428 (2001) 29-36.
[27] J. M. Macdougall, et al., Bioorg Med Chem 12 (2004) 5983-5990.
[28] E. Malatynska, et al., Neuroreport 6 (1995) 613-616.
[29] E. Malatynska, et al., J Pharmacol Exp Ther 278 (1996) 1083-1089.
[30] S. Dagar, et al., J Control Release 91 (2003) 123-133.
[31] T. Ishida, D. L. Iden, T. M. Allen, FEBS Lett 460 (1999) 129-133.
[32] M. Kates, Techniques in Lipidology, Elsevier, New York, 1972.
[33] H. G. Enoch, P. Strittmatter, Proc Natl Acad Sci U S A 76 (1979) 145-149.
[34] Z. Wang, J Neurosci 21 (2001) 1779-1786.
[35] D. J. Linden, Science 301 (2003) 1682-1685.
[36] M. A. Sutton, et al., J Neurosci 24 (2004) 3600-3609.
[37] J. W. Park, C. C. Benz, F. J. Martin, Semin Oncol 31 (2004) 196-205.
[38] L. H. Lazarus, et al., J Biol Chem 264 (1989) 354-362.
[39] M. Attila, et al., Int J Pept Protein Res 42 (1993) 550-559.
[40] D. Cocchi, et al., Life Sci 36 (1985) 1707-1713.
[41] P. L. Prather, et al., J Biol Chem 269 (1994) 21293-21302.
[42] S. Chakrabarti, et al., J Neurochem 64 (1995) 2534-2543.
[43] P. F. Zaratin, et al., J Pharmacol Exp Ther 308 (2004) 454-461.
[44] H. K. Kramer, Neuropharmacology 39 (2000) 1707-1719.
[45] J. A. Becker, et al., J Biol Chem 274 (1999) 27513-27522.
[46] P. J. Emmerson, et al., Eur J Pharmacol 494 (2004) 121-130.
[47] G. R. Uhl, I. Sora, Z. Wang, Proc Natl Acad Sci U S A 96 (1999) 7752-7755.

I claim:

1. A method to target a compound to a mu opioid receptor, the method comprising:
   (a) covalently conjugating a mu opioid receptor ligand to a PEGylated lipid that is DSPE-PEG$_{3400}$ (DSPE: 1,2-Distearoyl-sn-Glycero-3-Phosphoethanolamine) to form a conjugate; and
   (b) inserting the conjugate into a carrier for the compound, wherein the carrier is a nanoparticle that is a sterically stabilized liposome (SSL) and said conjugate is a surface ligand specific for the mu opioid receptor.

2. The method of claim 1 wherein the opioid receptor is a human mu opioid receptor (hMOR).

3. The method of claim 1 wherein the conjugate is DSPE-PEG$_{3400}$-dermorphin (DPD).

4. A composition comprising:
   (a) a mu opioid receptor ligand conjugated to a PEGylated lipid that is DSPE-PEG$_{3400}$(DSPE: 1,2-Distearoyl-sn-Glycero-3-Phosphoethanolamine);
   (b) a carrier, wherein the carrier is a nanoparticle that is a sterically stabilized liposome (SSL) with surface ligands specific for the opioid receptor; and
   (c) a compound to deliver to the mu opioid receptor.

5. A pharmaceutical delivery system to carry pharmaceutical agents to achieve repair-specific delivery of analgesics and/or alleviate side effects associated with mu opioids receptor activation, the system comprising:
   (a) a mu opioid receptor ligand conjugated to a PEGylated lipid that is DSPE-PEG$_{3400}$(DSPE: 1,2-Distearoyl-sn-Glycero-3-Phosphoethanolamine);
   (b) a carrier, wherein the carrier is a nanoparticle that is a sterically stabilized liposome (SSL) with surface ligands specific for the opioid receptor; and
   (c) the pharmaceutical agent.

6. The pharmaceutical delivery system of claim 5, wherein said delivery system is dermorphin-SSL.

7. A method to synthesize a DSPE-PEG$_{3400}$ conjugated dermorphin, the method comprising:
   (a) modifying dermorphin with a cysteine residue at the C-terminus; and
   (b) coupling of the thiol group of the modified dermorphin and the malemide of DSPE -PEG$_{3400}$-MAL.

* * * * *